(12) United States Patent
Dickinson et al.

(10) Patent No.: US 6,275,724 B1
(45) Date of Patent: Aug. 14, 2001

(54) MEDICAL ULTRASONIC IMAGING

(75) Inventors: Robert Julian Dickinson; Timothy Spencer, both of London; Anthony Stenning, Guildford, all of (GB)

(73) Assignee: Intravascular Research Limited, Isleworth (GB)

( * ) Notice: Subject to any disclaimer, the term of this patent is extended or adjusted under 35 U.S.C. 154(b) by 0 days.

(21) Appl. No.: 09/191,796

(22) Filed: Nov. 13, 1998

(30) Foreign Application Priority Data

Mar. 27, 1998 (GB) .................................................. 9806465

(51) Int. Cl.[7] ....................................................... A61B 5/00
(52) U.S. Cl. ............................................. 600/424; 600/466
(58) Field of Search ................................... 600/424, 466, 600/585; 606/130; 128/899; 324/207.11, 207.13

(56) References Cited

U.S. PATENT DOCUMENTS

| 4,834,725 | * | 5/1989 | Iwatschenko . |
| 5,353,354 | * | 10/1994 | Keller et al. . |
| 5,569,296 | * | 10/1996 | Marin et al. . |
| 5,593,431 | * | 1/1997 | Sheldon . |
| 5,868,673 | * | 2/1999 | Vesely . |
| 5,876,345 | * | 3/1999 | Eaton et al. . |
| 6,016,439 | * | 1/2000 | Acker . |
| 6,052,610 | * | 4/2000 | Koch . |
| 6,061,588 | * | 5/2000 | Thornton et al. . |

\* cited by examiner

Primary Examiner—Marvin M. Lateef
Assistant Examiner—Shawna J Shaw
(74) Attorney, Agent, or Firm—Richard M. Goldberg

(57) ABSTRACT

A method of measuring the position of the tip of a catheter includes the steps of continuously monitoring the distance the catheter has travelled past a reference point, monitoring the orientation of the tip, and reconstructing the trajectory of the catheter tip.

10 Claims, 6 Drawing Sheets

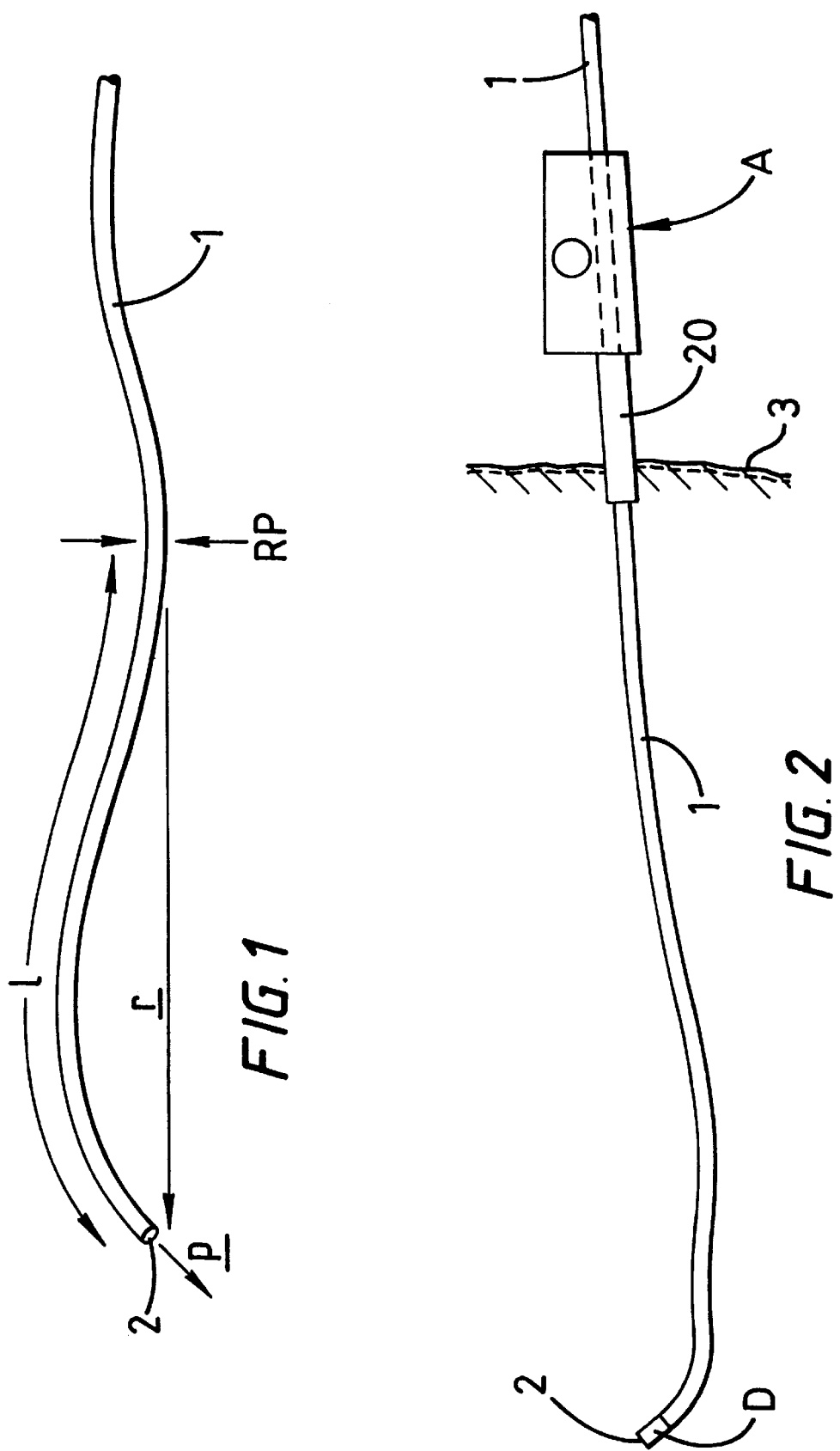

MEDICAL ULTRASONIC IMAGING

BACKGROUND OF THE INVENTION

The present invention relates to medical ultrasonic imaging and in particular to such systems which utilise a catheter insertable into a patient and carrying an ultrasonic transducer array at or near its distal end.

This invention relates to the use of catheters in medical practice, and in particular to using catheters for diagnosis and treatment in the heart, either in the chambers of the heart, or in the coronary arteries. In many procedures it is valuable to have information on the location of the catheter tip within the body. One example is in intra-vascular ultrasound imaging (IVUS) where by pulling back the catheter on a trajectory defined by a guide-wire the two-dimensional images can be stacked to give a three dimensional representation of the inside of the artery. Our UK patent 2,246,632 discloses such a system. In current methods the trajectory is assumed to be a straight line in the absence of other information, and so the representation may not faithfully represent the true three dimensional (3-D) shape of the vessel. Another example of such a procedure is electrophysiology, where the electrical signals of the heart are measured at a number of different positions around the heart wall, and the location of each measurement is important.

There are a number of techniques for position measurement, usually relying on external radiation. The position of the tip on two bi-plane X-rays has been used to calculate the tip position in three dimensions (3-D reconstruction from biplane-angiography by C. R. Moll IBM internal report UKSC124, September 1984). Another technique uses an ultrasound transmitter located in the catheter and external ultrasound imaging, (Bryer et.al. Medical and Biological Engineering and Computing, 268–271, 1985). Many techniques use low frequency magnetic fields to induce a signal in a coil mounted in the catheter, the amplitude of the signal being dependent on the position and orientation of the coil relative to the applied external magnetic field, examples of this method being described in U.S. Pat. No. 4,017,858, U.S. Pat. No. 5,042,486 and U.S. Pat. No. 4,045,881. A further example of this is PCT/US95/01103, where three transmit planar coils are placed on the patient bed, and three orthogonal receive coils placed in the catheter. By exciting the transmit coils at different frequencies, and appropriate analysis, the three spatial co-ordinates and three orientation angles of the catheter tip can be calculated.

There are a number of devices that attempt to measure or control the linear distance that a catheter is inserted into the patient. One example of a device that controls the catheter position by using the motor drive translation of the catheter in the body is given in WO94/00052, and an example of a device which measures the position is given in WO93/20876. These devices have the significant disadvantage that they have to be separated from the sterile field by a sterile drape.

SUMMARY OF THE INVENTION

The objectives of the present invention are to provide:
a) a system whereby the position/orientation of the distal tip of a catheter within a patients body can be sensed and identified:
b) a simple device for measuring or controlling the linear distance that a catheter is inserted into a patient.

With regard to a) above a system according to the present invention measures the tip orientation and the scalar trajectory length at points in time from a datum start position and from these calculates the three-dimensional shape of the tip trajectory and thus the tip position at any time.

This is possible because it has been recognised by the inventors that the orientation and position of the catheter tip are not independent if the time history is known because the catheter can only move along its axis when pushed over a guide wire.

The scalar trajectory: (i.e. the length which the catheter has been inserted into the patient) could be measured or controlled by a motor using a linear detector as disclosed in our co-pending application 9718984. However, the present invention is also concerned with providing a simplified device for this purpose.

According to the present invention such a linear detector is hand held, is incorporated in the same sterilised package as the catheter and is disposable with the catheter, and relies on manual driving of the catheter, i.e. no motor is involved as required with prior-art devices which rely on a steady predictable pull-back rate for their effective operation.

BRIEF DESCRIPTION OF THE DRAWINGS

How the invention may be carried out will now be described by way of example only and with reference to the accompanying drawings in which:

FIG. 1 illustrates diagramatically a typical curvilinear length of catheter;

FIG. 2 illustrations a catheter position sensor device in position at or near the proximal end of the catheter;

DETAILED DESCRIPTION

FIG. 1

Consider a curvilinear length of catheter 1 having a tip 2. If p is the unit vector of the tip orientation, r is the position of the tip2 relative to a fixed reference point and l is the length of the catheter1 from that reference point (FIG. 1) then for a given movement increment dl:

$$dr = p.dl$$

$$r(t) = \int_0^t p.dl = \int_0^t p(t)\frac{dl(t)}{dt}dt$$

Thus if the tip orientation and scalar trajectory length are known at all points in time from a particular start positionRP, then the 3d shape of the trajectory is calculable and the tip position at any time is also known. This assumes that:

i) the only changes in position are those caused by a movement along the trajectory, and ii) the trajectory the tip has previously passed over does not change.

Both these assumptions will be true for small movements such as when pulling a catheter back over a guidewire during an ultrasound examination. Thus to estimate position the time history of two pieces of information are required:

The scalar distance l(t) the catheter has moved past a reference point;

The orientation p(t) of the catheter tip against the laboratory frame of reference.

FIG. 2

FIG. 2 shows the arrangement to measure catheter position using a sensor device A which is described in more detail later with reference to FIG. 8, the patient's skin being indicated at 3, the sensor A being located outside the patient and the length of catheter 1 to the left of the patient's skin 3 being located within the patient.

The scalar distance can be easily measured by the device A located external to the patient measuring the distance travelled by the portion of the catheter external to the patient. This distance is equal to the distance travelled by the catheter tip, assuming that stretching or other distortion of the catheter is negligible and there is no slack to be taken up.

The orientation of the catheter tip is determined by an orientation sensor arrangement indicated at D and described in more detail later with reference to FIGS. 3 to 7.

Figure 8:
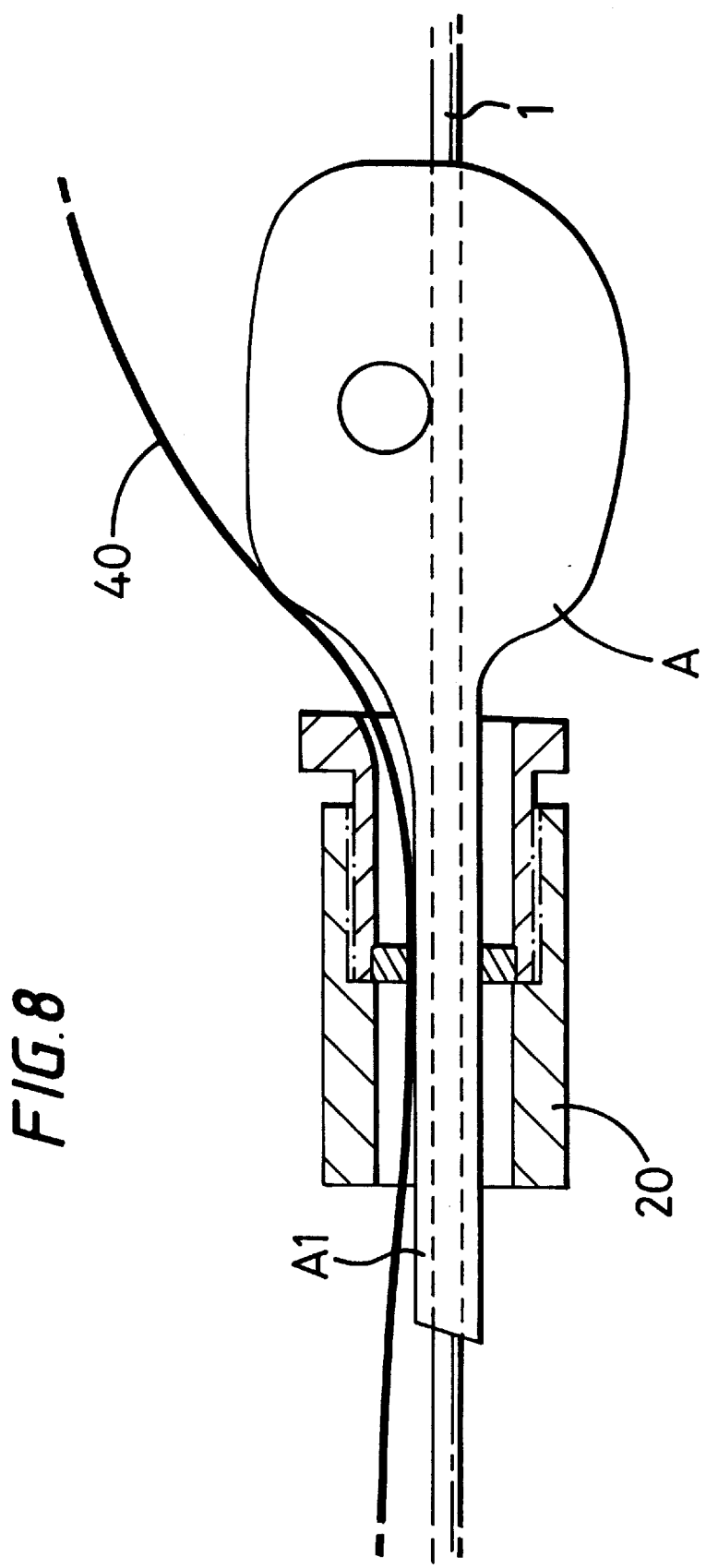
FIG. 8 is a diagramatic view of a pull-back device according to the present invention.
Figure 9:
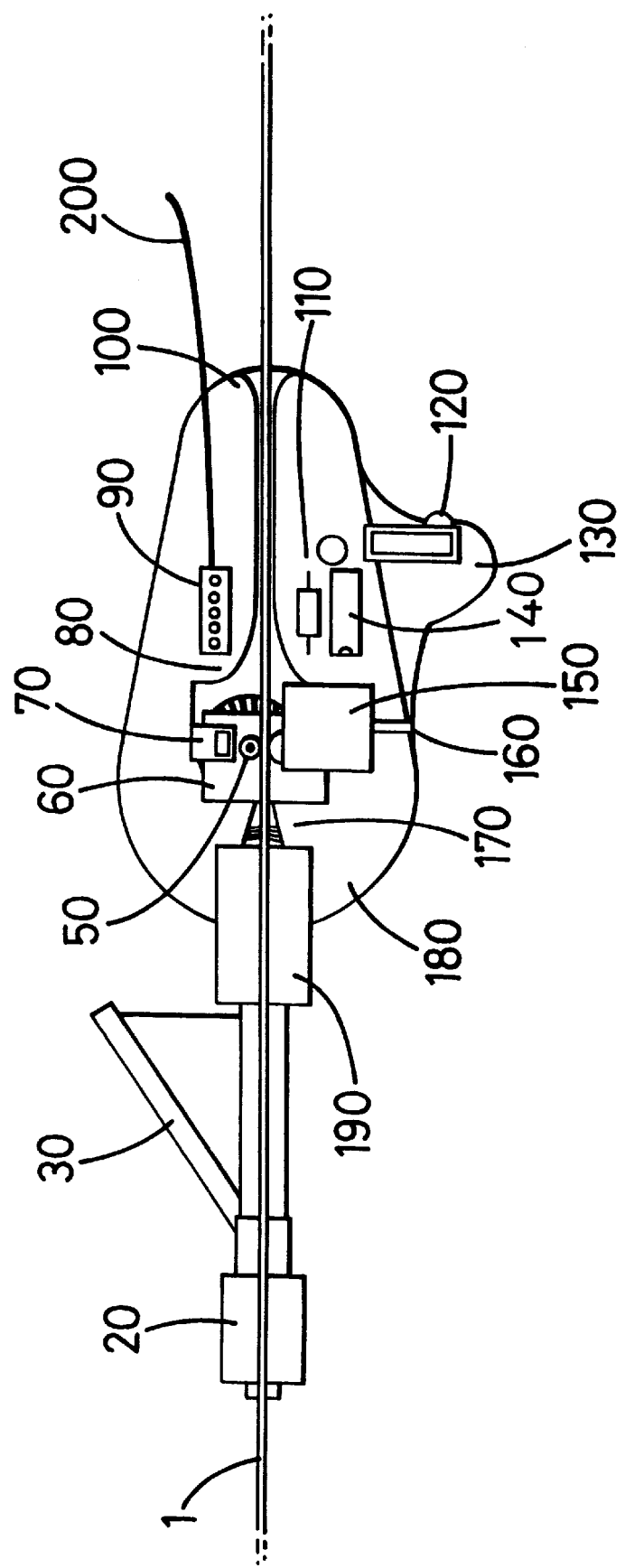
FIG. 9 is a plan-ghost view showing the pull-back device in more detail but with the extension tube-sheath A1 of FIG. 8 omitted.

FIGS. 8 and 9

This figures illustrates the catheter position sensor device A in more detail, this device being designed to be hand-held. The pull-back of the catheter is achieved manually by the clinician/operator, but an electrical connection to a signal processing unit enables positional information to be recorded, facilitating the display of 'distance travelled' on a CRT Screen and more accurate reconstruction of 3-d data sets and the potential of real-time display of longitudinal cross-sections to be achieved. Alternatively the distance travelled is indicated on a digital display mounted on the device A. As long as the operator pulls the catheter back within a reasonable range of speeds, the need for a motor's constant rate-of-pullback is largely made redundant by the transmission of positional/speed information to the imaging system. Although sacrificing smooth pull-backs, the omission of a motor has a number of advantages, one of the most important being that of a lighter, smaller unit.

The hand-held device A is included in the catheter packaging, being supplied as a sterile, single-use disposable unit. Having threaded the catheter 1 through the device A, it can be moved up to the vessel entrance sheath, where it will be held against a so-called Tuey valve 20. For power and communications, a slim cable 200 connects the device A to a catheter interface module or a similar unit which, in turn, will be connected to the signal processing unit.

As the catheter is moved relative to the unit A it detects the movement by means of a spindle 50 and wheel 150 which gently pinch the catheter 1. The rotation of the spindle 50 is encoded by an optical LCD transmitter/detector pair 70 mounted across a slotted wheel 60. The pluses generated by this circuit are processed by a mouse controller chip 140 which subsequently sends a serial stream of positional data to the catheter interface module (or its equivalent) and ultimately, is processed by the signal processing unit. In this way each image frame can be 'position-stamped'.

The catheter 1 is to be threaded through the device A at the beginning of the investigation which is left on the catheter for the duration of the study, being slid out of the way when not required for pull-back. The design of the pinch-roller mechanism 50, 150 is critical since the catheter 1 must be gripped without slippage, but not so much that there is resistance to catheter 1 movement or that the catheter 1 body is damaged in any way.

The sensor A has a tubular extension A1 through which the catheter freely moves. This tube is inserted into the Tuey valve that can be tightened to clamp down onto the tube hence preventing movement between the Tuey valve and the sensor. In catheters known as rapid-exchange or monorail devices the guide wire 40 will be positioned outside the catheter and outside the monorail devices and outside the tube A1, and is clamped to the tube when the Tuey valve is tightened. This allows the catheter to be moved without moving the guide-wire position. Alternatively the Tuey valve 20 and unit A could be integrated into a single unit.

All entrance apertures of the unit A must guide the catheter 1 gently into the desired position by means of smooth funnels, 80, 180, 170 preferable coated with Teflon or an equivalent low-friction coating. The catheter 1 is guided through the rollers 50, 150 with sufficient restriction of lateral movement to ensure that the catheter 1 cannot wander off from the central portion of the roller contact area.

The spindle 50 of the slotted wheel 60, which the catheter 1 must rotate as it moves through the device A, must have a high-friction surface to avoid slippage. To achieve this the spindle 50 has a rough surface and is coated with a rubber-like compound, or may have fine serration's around its circumference to increase its grip. The other important contribution to catheter-spindle friction is the diameter of the spindle 50. Although a larger radius will supply a greater contact surface area, a smaller radius spindle 50 will provide a greater sensitivity to movement for a wheel-encoder with a given umber of slots. A number of spindle-diameter slot-number combinations are given in Table 1 below along with the resulting position-measuring resolutions. A detailed knowledge of the surface properties of both the catheter 1 and spindle surfaces 50 and the pinching force supplied by the roller wheel 150 would be required to calculate the gripping characteristics of the mechanism. The choice of optimum spindle diameter 50 for a given encoder gradation will be done empirically. With finer slots in the encoder wheel 50 it must be ensured that the transmitter beam is not too wide so that it travels through more than one slot at a time.

| Spindle diameter (mm) | No. of slots in encoder wheel | Resolution (smallest unit of measurement) mm |
| --- | --- | --- |
| 2 | 20 | 0.075 |
| 2 | 30 | 0.500 |
| 2 | 40 | 0.040 |
| 3 | 20 | 0.120 |
| 3 | 30 | 0.750 |
| 3 | 40 | 0.060 |
| 4 | 20 | 0.160 |
| 4 | 30 | 0.100 |
| 4 | 40 | 0.075 |

There are two possible approaches to pinch wheel design 150. One option is to have a relatively hard material (e.g. nylon) for the wheel, which is forced against the catheter 1 by a sprung cantilever. The second approach is to have a pinch-wheel made of a softer material, like rubber, whose elastic properties (springiness) provides the pinching force. One of the advantages of the latter option is the ability of the soft material to accommodate any slight kinds or irregularities in the catheter 1. For either technique it is advantageous to be able to adjust the position of the pinch wheel 150, to provide a variable pinch force, so that the optimum contact pressure can be found empirically.

The free rotation of the encoder wheel is aided by the use of low friction materials at the point at which the spindle sits in the housing so that the use of lubricant oil is avoided. In order to prevent the required pinching force from damaging the catheter when not carrying out a pull-back a mechanism which can engage/disengage the spindle and roller may be provided.

In order to prevent the ingress of blood into the device A a set of brushes or a low friction valve may be provided at 170.

Ideally, the final longitudinal resolution of any 3-d data set should be between 0.1 mm and 0.2 mm between slices. Given that the slice thickness of the ultrasound beam is ~0.2 mm, then this 50% overlap gives parity with the axial and lateral resolutions of the ultrasound image. However, given the well documented error in this type of 3-d acquisition (without external 3-d catheter 1 tip location such as that calculated from angiography data) then this goal is inappropriate. A more realistic longitudinal resolution would be 0.5 mm. The position of frames captured within this period can be considered to be equidistantly spaced (i.e. that the catheter 1 can be considered to be moving at a constant velocity over this small range).

The cable connecting the Unit A to the signal processing unit needs to be light so that it does not weigh down the catheter 1 more than the unit A itself. In FIG. 9 a five wire connection 90 to the cable 200 is used but a four wire connection may well suffice. The cable is also supplied sterile. The body 100 of the unit A is designed for easy grip by the operator's hand and facilitates the maintenance of a stable contact between the Unit A and the Tuey valve 20. A reset button 120 (microswitch) is mounted on the thumb grip 130 so that it can be operated by the thumb of the operator's hand, allowing the other hand to remain holding the catheter 1. This reset sets the distance measure to zero. The guide wire travels through the same value as the catheter, but not through the position sensor. The electronic components within the unit A are indicated at 110. The pinch roller unit 150 is provided with a spring tension adjusting screw 160.

FIG. 3

In a first method the orientation of the catheter tip 2 is measured using a 3-axis solid state gyroscope mounted to the catheter tip. Gyroscopes will determine changes in orientation from the original orientation, and hence by integrating over time the orientation vector p can be established. Small solid state gyroscopes can be constructed using vibrating sensors, (reference to be added). Examples of suitable devices are the ENV-05A GYROSTAR piezo gyroscope manufactured by Murata, that gives a signal proportional to angular velocity. The gyroscope is mounted using known die mounting techniques.

If the gyroscope assembly 4 consists of three mutually perpendicular gyroscopes giving outputs $U_\theta$, $U_{100}$, $U_\omega$ respectively $$\text{define: } \underline{U} = (U_\theta, U_\phi, U_\psi)$$

then $$\underline{U}.(t) = c.\underline{\omega}(t)$$

$\omega$ = angular_velocity $$\underline{p}(t) = \underline{p}_0 + \frac{1}{c}\int_0^t \underline{U}(t)dt$$

$p_0$ = initial_orientation c is a calibration constant of the gyroscope device.

Figure 3:
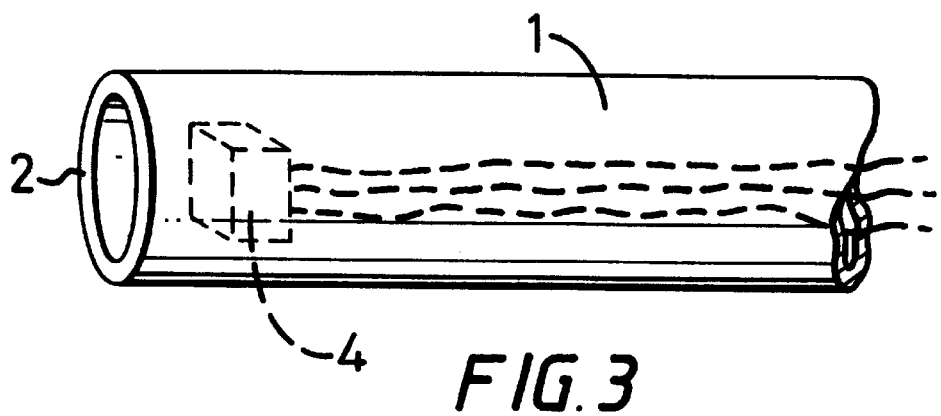
FIG. 3 illustrates the use of gyroscopes to detect the orientation of the catheter tip.
Figure 4A:
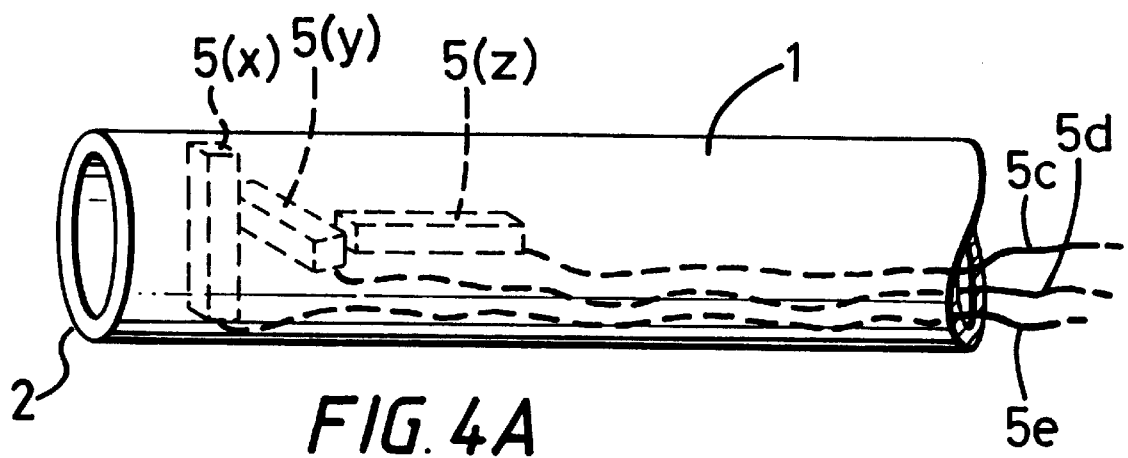
FIGS. 4a and 4b illustrates the use of accelerometers to detect the orientation of the catheter tip.
Figure 4B:
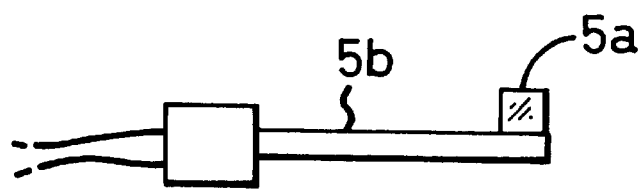

FIGS. 4A and 4B

A second method of detecting the orientation of the tip 2 of the catheter is to use a three-axis accelerometer assembly 5(x), 5(y) 5(z) mounted in the tip. The accelerometer assembly 5 can be based on known designs of micro-machined silicon cantilevers (5a, 5b), which are miniaturised to fit inside a catheter 1 of diameter 1–2 mm. If then a small acceleration to the whole body is a known direction is applied, then by standard vector component algebra the orientation of the accelerometers and hence that of the catheter 1 tip relative to the acceleration can be calculated. The acceleration can be generated by a series of very small displacements, or by a small amplitude sinusoidal vibration. The displacement can be less than 0.1 mm and still generate sufficient acceleration to produce an adequate signal from the accelerometer. The amplitude of the vibration is not important as long as the direction is pre-determined. In another embodiment, no external acceleration is required and the accelerometer is used to measure the force produced by the weight of the accelerometer mass. which is always in the vertical direction. This has the advantage that no modifications to the patient bed are required. In effect the accelerometer arrangement acts as a plumb line inside the catheter 1, allowing the continual monitoring of the vertical direction. An example of a suitable accelerometer is the ADXL05 manufactured by Analog Devices, Norwood, Mass. 02063-9105. This device is supplied packaged and in the design described here the unpackaged silicon die is mounted on the catheter 1 using known multi-chip module techniques. An example of a mounting technique of a die in a catheter 1 is given in our published UK patent application No. 2,287,375.

FIG. 5

A third method applicable to the pull-back of a catheter 1 in an artery 6 relies on the principle that the orientation changes when the catheter 1 turns a corner, when the outside of the curve will travel past at a greater speed than the inside. The fluctuations of ultrasound echoes, signals A and B in FIG. 5 can be used to estimate the velocity of tissue past the catheter 1.

One of the main sources of error in the reconstruction of 3-D pull-back sequences is the non-linear relationship between the movement of the catheter body 1 as it is pulled at the proximal end and the corresponding displacement of the imaging tip 2 at the distal end. Regardless of whether the catheter 1 is pulled back by a stepper-motor (step pitch known), D.C. motor, or by hand, any positional information is derived from a measurement of linear displacement at the catheter 1 entrance point (femoral artery). However accurately this measurement may be carried out, the technique assumes that each linear 'pull' of the catheter 1 translates to a linear movement of the same magnitude at the tip. Due to the tortuous path of the catheter 1 and the likely occurrence of slack, significant errors are likely in the estimation of the tip movement. Moreover, any movement through a bend will still be reconstructed, in error, as a linear section of vessel.

Current techniques for detecting the tip position in 3-dimensional space rely on the use or orthogonal angiographic data and are both computationally intensive and relatively crude in their location of the catheter 1.

Figure 5:
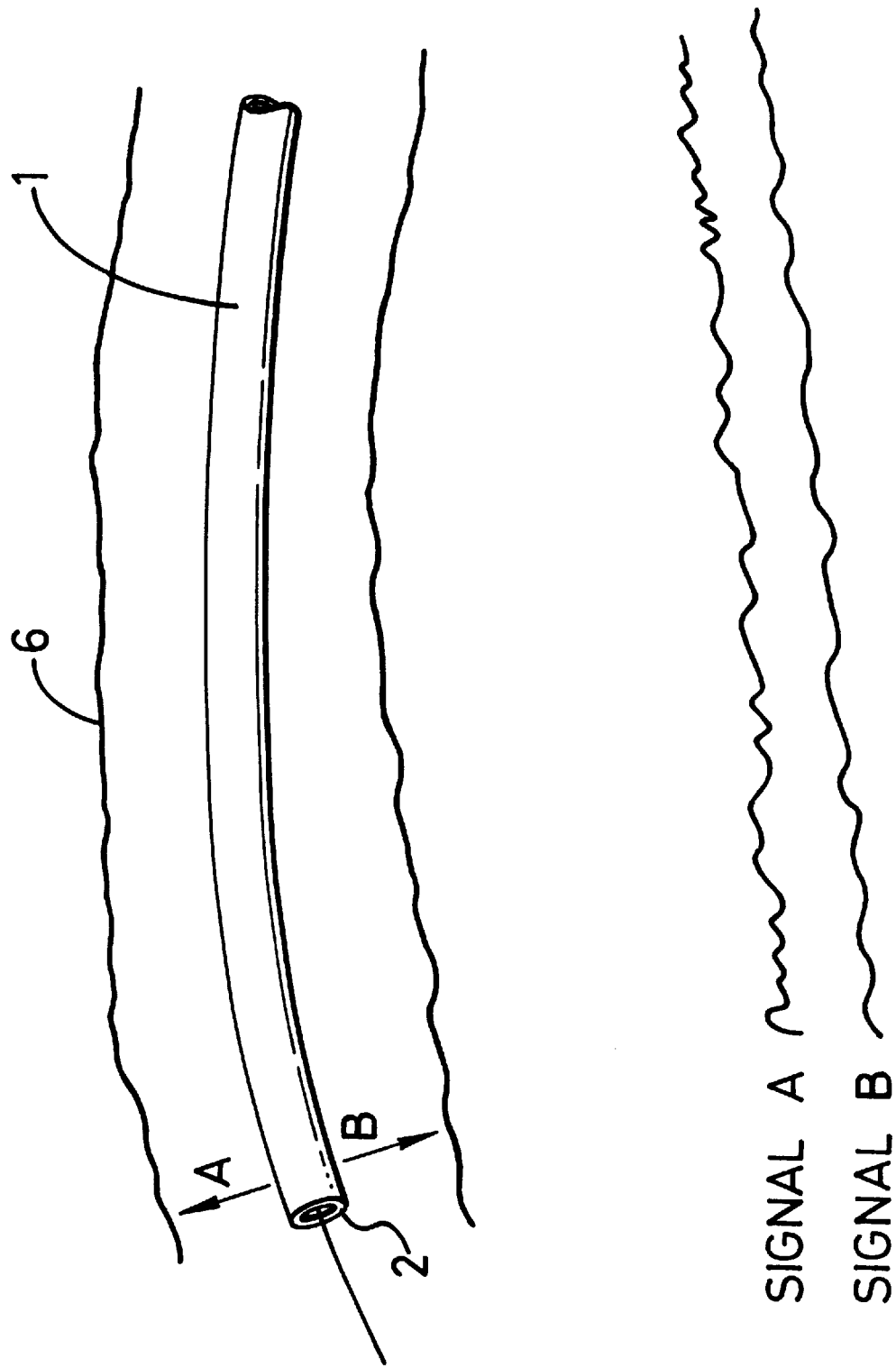
FIG. 5 illustrates the use of the fluctuations in the ultrasound echoes to determine the orientation of the catheter tip.

In the embodiment of the invention illustrated in FIG. 5 it is proposed to accurately record the catheter 1 tip position by processing the ultrasound signals received by the imaging array. By comparing consecutively-fired A-scan lines at one position in the array, it is possible to detect and quantify any changes in the signal over time. In this context, such signal changes in the vessel wall are most likely to be caused by displacement of the scatterer volume with respect to the beam. This displacement could be due to the physiological contraction and dilation of the vessel during the cardiac cycle (which may also cause slight movement of the tip with respect to the vessel) or the longitudinal movement of the catheter 1 during a pullback. Within the lumen, the passing of red blood cells (RBCs) will also disrupt the signal between successive A-scan lines, due to the constant transit of RBC scatters through the ultrasound beam.

The detection of scatterer displacement could be done by cross-correlation or speckle-tracking techniques. In either case, the section of each A-scan corresponding to the vessel wall signal would have to be identified and from such sections the algorithm would have to be able to discriminate between changes in back-scatter due to the longitudinal movement of the catheter 1 (pullback) and changes due to other effects (vessel pulsatility and non-longitudinal movements).

The classical approach to the comparison of A-scan data and the most commonly used, is that of cross-correlation. The correlation coefficient has been used extensively in calculating strain within the vessel wall ('elasticity imaging') and recently the decorrelation rate of the RBC scatters within the lumen has been used to map blood flow using RF data from IVUS probes. In the latter application the signal decorrelation due to the passing blood is many times greater than that of the vessel wall (time constants: $Tc_{(blood)}$–1 msec c.f. wall>>6 msec). This enables signals within the lumen to be segmented with minimal error. The sources of decorrelation in the remaining section of signals would have been due to a combination of the following wall motion (the same scatterers moving axially within the beam in sympathy with the cardiac cycle); wall compression/expansion (a change in the density of scatters over the cardiac cycle); noise (random changes in amplitude and phase); transducer beam characteristics; and any longitudinal movement of the catheter 1 (new scatterers entering/old scatters leaving the beam volume).

Assuming a concentrically positioned catheter 1, the scatterer effects due to vessel pulsatility will, theoretically, only manifest themselves as axial decorrelation (i.e. along the direction of the beam); wall movement (~1 $mm,s^{-1}$) will produce a phase shift in the A-scan resulting in a large decorrelation component. Therefore, A-scan lines have to be phase-matched before the correlation coefficient is calculated. Compressional changes will cause local phase and amplitude changes in the signal as scatterer spacings change over the cardiac cycle. This too will contribute to de-correlation but, unlike the wall motion artefact, will not be removed by straightforward phase-matching. However if ECG-gating is used to select frames during diastole, then the effect of wall motion and wall compression should be minimised.

Having phase-matched the RF lines then the cross-correlation coefficients are calculated within common overlapping range-gated windows. For blood flow mapping there is a trade-off between short windows (to increase the spatial resolution of the final parametric image and to limit the effect of the velocity gradient inherent in parabolic flow) and longer windows (less error in de-correlation estimation). The application of this technique to detect longitudinal catheter motion requires only that an estimation of pull-back speed be calculated for each of four axial positions (north, south, east and west). Since no image is required to be made with this data, then a longer window is more appropriate and should vive a more accurate measure of the correlation coefficient. The only disadvantage with having a single long window is that the decorrelation measure on a tight corner will effectively be derived from the average of small displacements at the vessel lumen and larger displacements at a greater depth.

For the measurement of lateral scatterer movements a calibration has to be carried out for the transducer, since the decorrelation slope for lateral displacements is range dependent (due to the beam profile). The use of a phased-array device has the potential benefit in having more uniform beam characteristics, particularly with regard to the axial intensity profile in the near field. A further benefit of measuring decorrelation in the vessel wall, as opposed to within the lumen, is that measurements in the very near field will be avoided for all but very eccentric catheter 1 positions, avoiding the influence of side-lobe and catheter-to-catheter beam variations.

It is stipulated that a signal-to-noise ratio of the imaging system of greater than 20 dB is required if correlation errors of less than 10% are to be achieved.

The measurement of pull-back speed using the decorrelation technique would essentially be exploiting the same phenomenon as is measured in the blood flow application, the lateral displacement of scatterers across the ultrasound beam. Although the rate of lateral displacement for a pull-back would be orders of magnitude slower, both applications require the removal of contributions from other sources of signal decorrelation. Phase-matching of successive A-scan lines will be essential to remove axial decorrelation due to wall motion, but some degree of ECG-gating is necessary to avoid the likely decorrelating effects of tissue compression during systole, since it will cause an increase in scatterer density.

The segmentation of the vessel wall from the lumen should be provided by the decorrelation measurement itself, given that the rates are significantly different. In vivo blood flow experiments have shown a decorrelation time constant (time for correlation function to fall to $\frac{1}{10}$) for blood to be 1 msec, compared with a value of >>6 msec for the vessel wall (chosen during diastole when there was minimal vessel contraction/dilation). Experimental implementations of the blood flow measurement technique have used pulse repetition frequencies (PRFs) of 4 KHz to 5 kHz which have aimed to measure standard physiological blood flows of 40–80 cm/s. Assuming a loosely linear relationship between the velocity of the target and the PRF that is required to quantify this, a pull-back speed of 1 mm/s could be detected with PRFs as low as 10 Hz–13 Hz. Given a PRF of 30 Hz, pull back speeds up to ~4 mm/s should be able to be measured at a similar resolution. If this implementation was successful then pull-back sequences captured with a frame rate of 30 Hz could be processed, off-line, to enable their correct 3-dimensional reconstruction. By calculating displacements at each time interval in the four compass directions (north, south, east and west) then the orientation of the catheter 1 with respect to the lumen can be ascertained. This will enable vessel bends to be reconstructed properly since outer curvatures will produce greater displacements than inner surfaces.

Although possibly not as accurate, the demodulated 1-signal could be used for cross-correlation calculations instead of the raw received signal.

Figure 6:
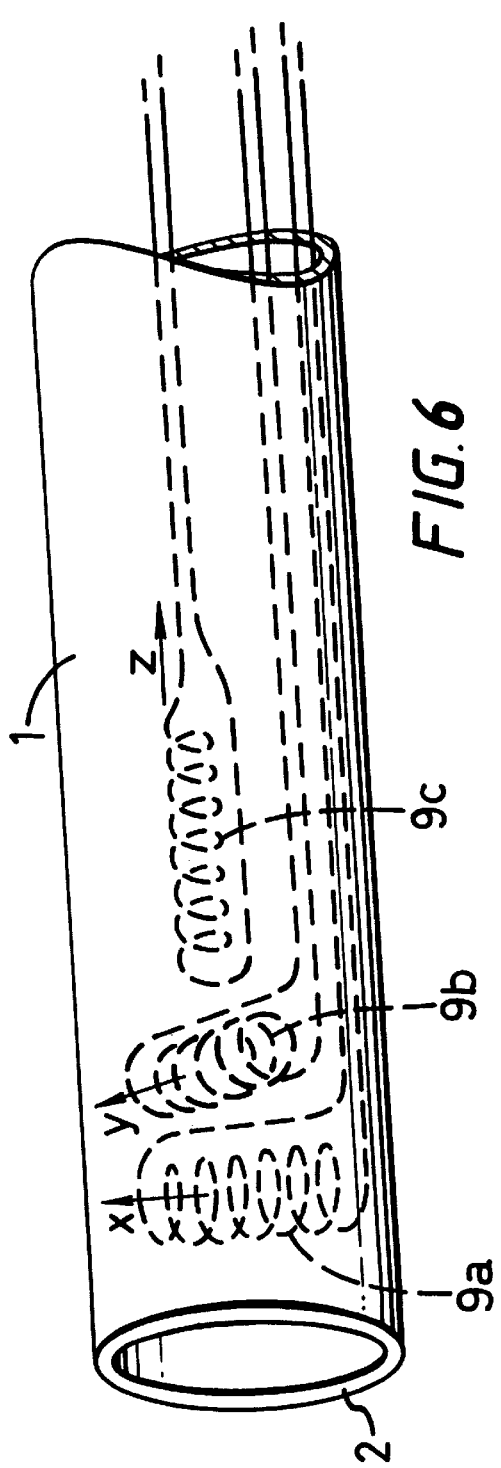
FIG. 6 illustrates a first use of magnetic fields to measure the catheter tip orientation.
Figure 7:
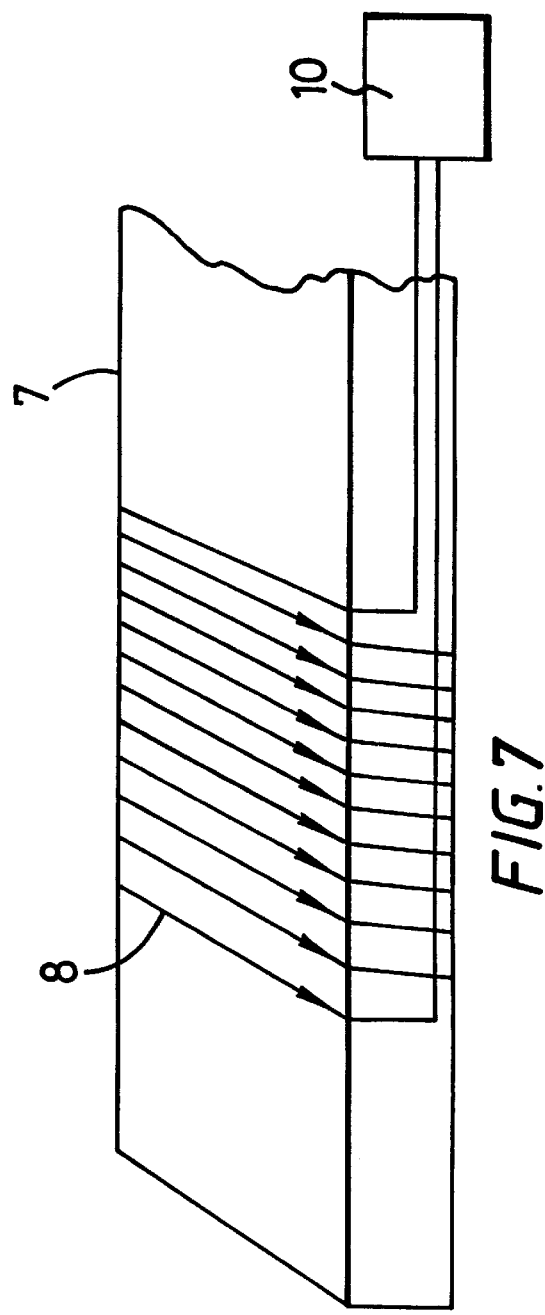
FIG. 7 illustrates a second use of magnetic fields to measure the catheter tip orientation.

FIGS. 6 and 7

A fourth method of measuring the orientation of tip 2 is to use magnetic fields. The present invention measures the magnetic field orientation only, so the requirements on the field are only to have a uniform vector direction. The patient (not shown) lies on a bed 7 which is provided with an electrical coil arrangement 8 powered by a generator 10 and designed to produce a uniform current sheet having a uniform vector direction.

Fields with a uniform vector direction can easily be generated for example by the arrangement disclosed in UK patent 2 226 138.

The tip 2 of the catheter is provided with an arrangement of three coils 9a, 9b and 9c positioned mutually orthogonally in directions x, y and z. The way in which the field generated by the coil 8 couples with the coils 9a, 9b, 9c is described in U.S. Pat. No. 4,017,858 U.S. Pat. No. 4,045,881 and PCT/US95/01103. The current sheet 8 produces a field parallel to the bed 7, and couples with the three perpendicular coils 9a, 9b, 9c mounted in the catheter tip 2. Alternatively two bed mounted coils could be used which produce perpendicular fields, which are distinguished by exciting at different frequencies. The orientation vector can then be established by two coils in the catheter 1.

What is claimed is:

1. A pull back device comprising a hand-held unit adapted to have a catheter passed therethrough and to be drawn therethrough by hand, the unit including:
   a pinch-roller mechanism comprising a spindle for guiding the catheter;
   a device which generates a signal in response to rotation of the spindle indicative of a length of the catheter that has passed therethrough;
   an arrangement adapted to be mechanically connected to a Tuey valve in a manner to prevent movement therebetween; and
   an electrical connection adapted to transmit the signal to a data processor.

2. A pull back device as claimed in claim 1 wherein the arrangement comprises a tubular extension arranged to have a valve clamped thereto.

3. A pull back device as claimed in claim 2 in which the hand-held unit is provided with a seal arrangement to prevent ingress of blood into the unit when in use.

4. A pull back device as claimed in claim 1 in which the hand-held unit is pre-mounted on the catheter.

5. A pull back device as claimed in claim 1 in which a guide wire is fixed in position external to the hand-held unit.

6. A method of measuring the position of a tip of a catheter, comprising the steps of:
   generating a first data set of signals indicative of a distance a proximal end of the catheter which is outside of a patient has traveled past a reference point to provide a scalar trajectory length of the proximal end of the catheter;
   generating a second data set of signals indicative of an orientation of the distal end of the catheter to provide a trajectory vector direction of the distal end of the catheter; and
   combining the first and second data sets to construct a representation of a trajectory of the distal end of the catheter.

7. A method as claimed in claim 6 in which said step of generating a second data set of signals includes the step of monitoring the orientation of the tip by means of signals from gyroscopes mounted at or near a distal end of the catheter.

8. A method as claimed in claim 6 in which said step of generating a second data set of signals includes the step of monitoring the orientation of the tip by means of signals from accelerometers mounted at or near a distal end of the catheter.

9. A method as claimed in claim 6 in which said step of generating a second data set of signals includes the step of monitoring the orientation of the tip by detecting bends in the catheter using fluctuations in echoes from a patient's artery.

10. A method as claimed in claim 6 in which said step of generating a second data set of signals includes the step of monitoring the orientation of the tip by creating a magnetic field in an area of the tip and detecting variations in the magnetic field as a result of changes in the orientation of the tip.

\* \* \* \* \*